(12) United States Patent
Tajima et al.

(10) Patent No.: US 7,160,510 B2
(45) Date of Patent: Jan. 9, 2007

(54) OPERATION CHECKING DEVICE AND CHECKING METHOD FOR DISPENSER

(75) Inventors: Hideji Tajima, Matsudo (JP); Kimimichi Obata, Matsudo (JP); Hermann Leying, Mannheim (DE); Claus Bamberg, Mannheim (DE); Volker Degenhardt, Mannheim (DE)

(73) Assignees: Precision System Science, Co., Ltd., Chiba (JP); Roche Diagnostics GmbH, Mannheim (DE)

( * ) Notice: Subject to any disclaimer, the term of this patent is extended or adjusted under 35 U.S.C. 154(b) by 626 days.

(21) Appl. No.: 10/169,474

(22) PCT Filed: Dec. 27, 2000

(86) PCT No.: PCT/JP00/09335

§ 371 (c)(1),
(2), (4) Date: Sep. 17, 2002

(87) PCT Pub. No.: WO01/48487

PCT Pub. Date: Jul. 5, 2001

(65) Prior Publication Data

US 2003/0075556 A1    Apr. 24, 2003

(30) Foreign Application Priority Data

Dec. 28, 1999  (JP)  ................... 11-372308

(51) Int. Cl.
G01N 21/00  (2006.01)

(52) U.S. Cl. ........................................ 422/67
(58) Field of Classification Search ............ 422/67
See application file for complete search history.

(56) References Cited

U.S. PATENT DOCUMENTS

| 4,271,123 A | * | 6/1981 | Curry et al. ............... 422/64 |
| 5,637,275 A | | 6/1997 | Carey et al. |
| 5,653,940 A | | 8/1997 | Carey et al. |
| 5,679,948 A | | 10/1997 | Carey et al. |
| 5,741,708 A | * | 4/1998 | Carey et al. ............... 436/49 |
| 5,895,631 A | | 4/1999 | Tajima |
| 6,599,476 B1 | * | 7/2003 | Watson et al. ............. 422/63 |

FOREIGN PATENT DOCUMENTS

| JP | 58-154664 | 9/1983 |
| JP | 61-262639 | 11/1986 |
| JP | 02-061557 | 3/1990 |
| JP | 04-328467 | 11/1992 |
| JP | 07-035758 | 2/1995 |
| JP | 07-218397 | 8/1995 |
| JP | 07-287018 | 10/1995 |
| JP | 10-206214 | 8/1998 |

OTHER PUBLICATIONS

ISA/Japanese Patent Office, International Search Report for PCT/JP00/09335, dated Apr. 17, 2001, 4 pages.

* cited by examiner

Primary Examiner—Jill Warden
Assistant Examiner—Natalia Levkovich
(74) Attorney, Agent, or Firm—Haynes and Boone, LLP

(57) ABSTRACT

An object is to provide a dispenser operation verification apparatus and verification method that enables operation with high reliability and high accuracy.

The construction is such that with a dispenser comprising: one or a plurality of transparent or semi-transparent liquid passages capable of liquid suction, discharge and storage; a pressure control device for controlling the pressure in the liquid passage; a transport device for effecting relative movement between a container and the liquid passage; and an operation instruction device for issuing operating instructions to the pressure control device and the transport device, the operation of the dispenser is verified by providing; a detecting device for detecting an optical condition of the liquid passage, a movable region thereof or a part of that region, and a judgement device for judging the result of the instruction related to the liquid passage issued by the operation instruction device, based on the optical conditions detected by the detecting device.

35 Claims, 12 Drawing Sheets

Fig. 4
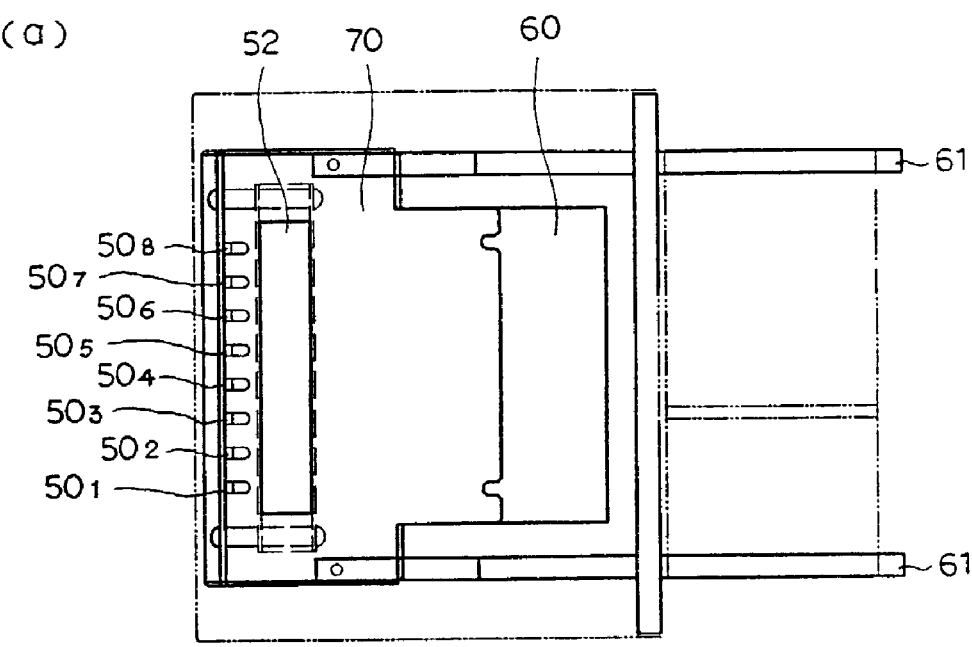
(a)
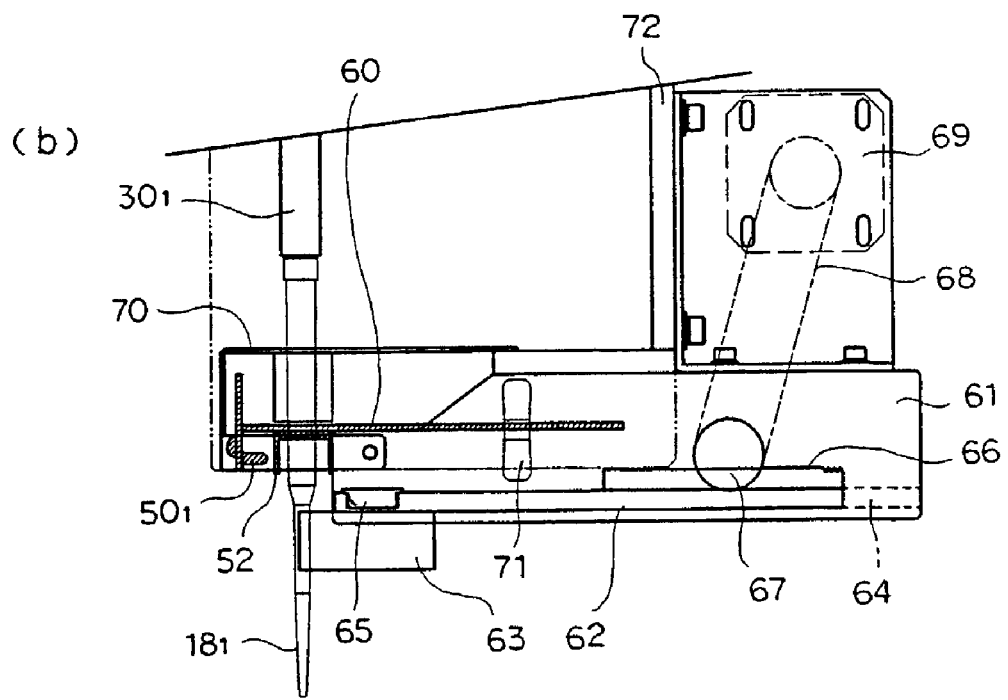
(b)

Fig. 6
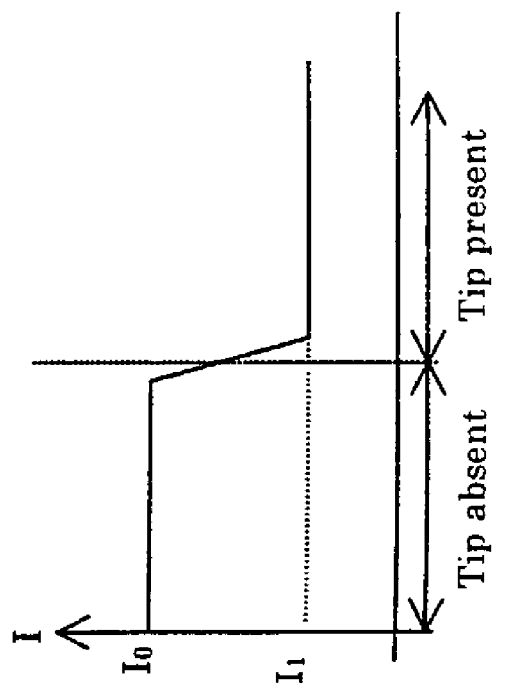
(C)
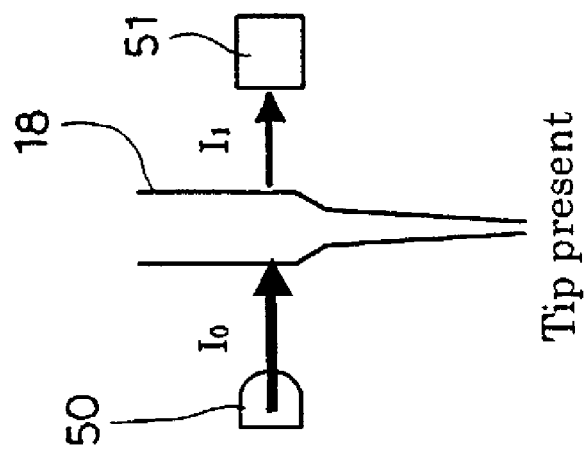
(b)
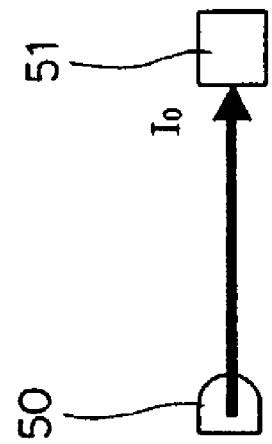
(a)

Fig. 7
(a)
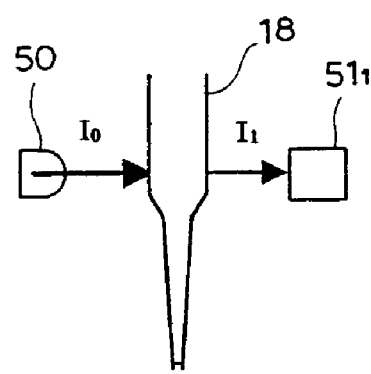
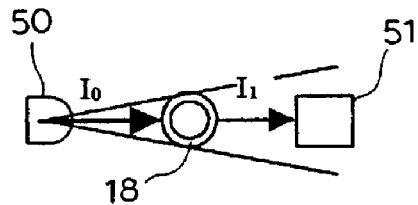
Liquid absent
(b)
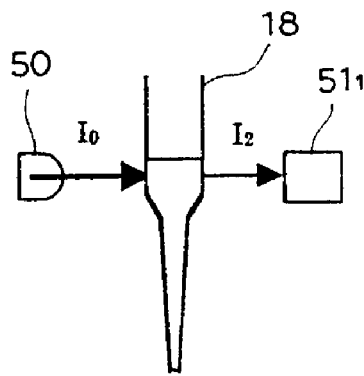
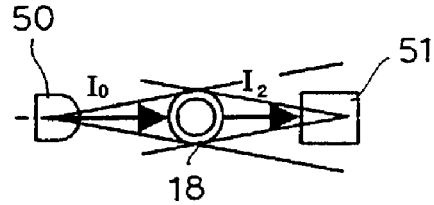
Liquid present
(c)
In the case of high light transmissivity liquid
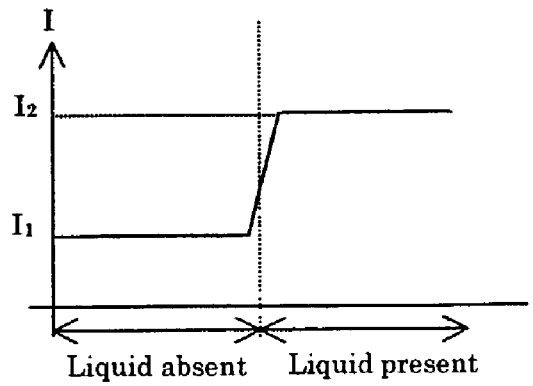
(d)
In the case of low light transmissivity liquid
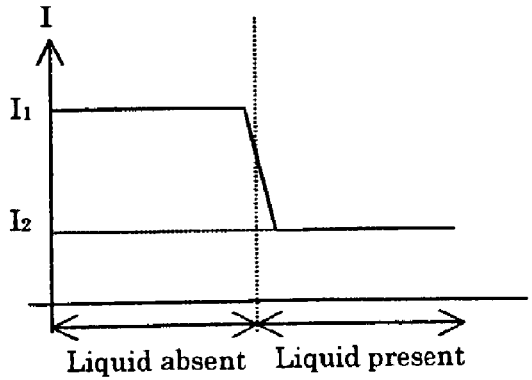

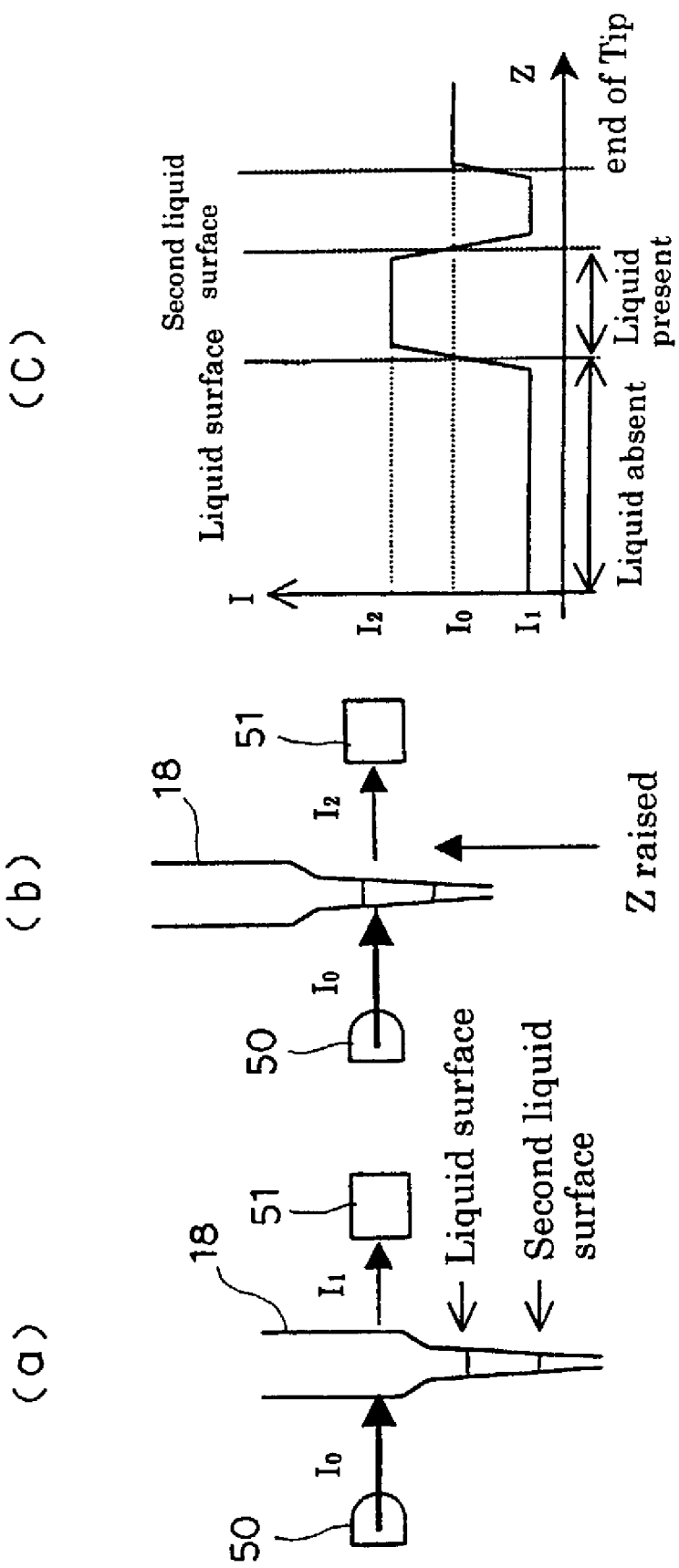

OPERATION CHECKING DEVICE AND CHECKING METHOD FOR DISPENSER

This application is a national phase filing of international application No. PCT/JP00/09335, filed Dec. 27, 2000, which claims priority to Japanese patent application No. 11-372308, filed Dec. 28, 1999.

TECHNICAL FIELD

The present invention relates to a dispenser operation verification apparatus and verification method, and more specifically relates to an operation verification apparatus and operation verification method for a dispenser provided with one or a plurality of transparent or semi-transparent liquid passages capable of the suction, discharge and storage of liquid The present invention is for performing high accuracy operations or processes with high quantification using a dispenser in various fields such as those fields which require the treatment of minuscule amounts of liquid, for example, the engineering field; the medical fields of hygiene, health, immunity, disease, genetics and the like; the agricultural science fields of food, agricultural products, marine products processing and the like; the science fields of biology, chemistry and the like; the pharmaceutical field and the like. The dispenser is for performing various operations and processes regarding liquids such as reagents or the like using a pipette tip or a nozzle. The working or operation of the dispenser include not only the suction and discharge of liquid, but also storage, agitation, transfer, separation, suspension, mixing and purification.

BACKGROUND ART

Heretofore, verifying whether the operation result or working result of a dispenser corresponds to the instruction of the user or not is performed by eye, using graduations or the like attached to a pipette tip or the like, or at most only by measurement of the air pressure in a pipette tip by a pressure sensor installed in the dispenser to detect lack of suction, liquid level and tip blockage.

Furthermore, in the case where a process is carried out by automated equipment that performs a series of operations sequentially and automatically, after the series of operations finishes, the verification has been done by no more than measuring the final liquid amount or the like obtained, and the operation has not been verified at each step during the process nor automatically.

PROBLEMS TO BE SOLVED BY THE INVENTION

Accordingly, there are problems that examination by eye is a big burden on the user, and also verifying whether the amount of suction, the amount of discharge or the like is correct or not cannot be performed accurately by eye.

Furthermore, there is another problem in that since measurement by a pressure sensor requires an air gap in the pipette tip, even if trying to perform a minuscule, quantified amount of dispensing (1–5 μliter), high accuracy quantification cannot be ensured. Moreover, there is another problem in that the condition of the pipette tip cannot be determined adequately or accurately by measuring only the air pressure in the pipette tip.

Furthermore, there is another problem in that the structure of the nozzle becomes complicated because the pressure sensor is installed so as to contactingly communicate with the pipette tip.

Moreover, since it is not easy to verify which malfunction has occurred, and in which operation, by only measuring the final liquid amount after a series of operations is finished, especially in a process that requires the accurate treatment of a minuscule amount; even a small difference in the liquid amount or the like by a small malfunction becomes compounded by further operations, and there is a possibility of obtaining, in the end, an extreme variance in the amount of liquid or the like from that initially planned, so that there is a problem in that verifying the operation needs to be performed automatically at each step.

Therefore, the present invention is aimed at solving the above mentioned problems, and a first object is to provide a dispenser operation verification apparatus and a verification method that improves the reliability and accuracy of the dispenser by verifying whether the dispenser is operating as instructed or not.

A second object is to provide a dispenser operation verification apparatus and verification method that can verify the operation of the dispenser automatically, promptly, efficiently and accurately, without any human intervention.

A third object is to provide a dispenser operation verification apparatus and a verification method which enables the dispenser to perform high accuracy processes quantitatively, and accordingly qualitatively, by verifying the operation of the dispenser, especially when treating genetic materials such as DNA or the like, bio-polymers of immune substances or the like and minuscule amounts of bio-compound liquid or the like.

A fourth object is to provide a dispenser operation verification apparatus and a verification method that performs verification of the dispenser operation with high reliability regarding whole processes consisting of a series of operations, by performing the operations while verifying the operation of the dispenser.

A fifth object is to provide a low-cost dispenser operation verification apparatus and verification method, which has a simple construction and can perform easy and reliable verification by detecting the operation of the dispenser remotely, without needing to interact directly with the inside of the liquid passage in the way that a pressure sensor does

DISCLOSURE OF THE INVENTION

To solve the above problems, a first aspect of the invention is that, with a dispenser comprising; one or a plurality of transparent or semi-transparent liquid passages capable of liquid suction, discharge and storage, a pressure control device for controlling the pressure in the liquid passage, a transport device for effecting relative movement between a container and the liquid passage, and an operation instruction device for issuing operating instructions to the pressure control device and the transport device, the operation of the dispenser is verified by providing; a detecting device for detecting an optical condition of the liquid passage, a movable region thereof or a part of that region, and a judgement device for judging the result of the instruction related to the liquid passage issued by the operation instruction device, based on the optical conditions detected by the detecting device.

Here, the liquid passage corresponds to a nozzle provided on the dispenser, a tip detachably mounted on the nozzle or both the nozzle and the tip detachably mounted on the nozzle.

In the case of "relative movement between a container and the liquid passage", there are cases where the container moves with the liquid passage fixed, where the liquid passage moves with the container fixed, and where both move. To be specific, "the judgement device" is comprised of a CPU, a memory device, a data display, a data output device for outputting a signal to another device, and the like.

According to the first aspect of the invention, the dispenser is provided with a detecting device for detecting the optical condition of the liquid passage, a movable region thereof or a part of that region, and a judgement device for judging the result of the instruction related to the liquid passage issued by the operation instruction device, based on the optical conditions detected by the detecting device.

Accordingly, regarding the operation of the dispenser, highly reliable and accurate verification can be performed at each operation. Furthermore, the operation of the dispenser can be verified automatically, promptly and efficiently, without any human intervention. By verifying the operation of the dispenser according to the present invention, especially when treating genetic materials such as DNA or the like, bio-polymers of immunity substances or the like and minuscule amounts of bio-compound liquid or the like, high accuracy processes can be performed quantitatively and, accordingly, qualitatively. Moreover, by performing the operations while verifying the operation of the dispenser, verification of the dispenser operation regarding the overall processing consisting of a series of operations can be performed with high reliability. Furthermore, the operation of the dispenser can be easily verified because of its simple structure, which provides a low cost dispenser operation verification apparatus and verification method.

Especially, according to the present invention, since the condition of the liquid passage is detected and judged optically, and not judged by the measurement of the pressure in the liquid passage, it is not necessary to draw air into the liquid passage, and hence, if the liquid is drawn up to the full capacity of the liquid passage, extremely high quantification can be obtained. Furthermore, since the condition is judged optically, various kinds of operation can be verified.

A second aspect of the invention is that with the first aspect of the invention, the judgement device judges the result of the instruction, based on information besides the optical condition, selected from amongst information containing; operation information related to the operation instructions of the operation instruction device, object information related to objects which the dispenser draws in, discharges and stores, and device information related to the dispenser including the liquid passage.

According to the second aspect of the invention, accurate and highly reliable verification of various aspects of operation can be performed, since the judgement device judges the result of the instruction, based on information besides the optical condition, selected from amongst information containing, the operation information, the object information and the device information.

A third aspect of the invention is that with the second aspect of the invention, the operation information contains: suction amount or discharge amount; presence of suction or discharge; speed of suction or discharge; suction and discharge operation including time of suction or discharge; and/or information on movement operation including movement path, movement direction and/or movement distance, the object information contains the kind or nature of liquid and/or the type and/or the presence of suspensions such as magnetic particles and the like, and the device information contains the nature and shape of the liquid passage and/or information showing the relationship between the distance from a suction aperture and the capacity of the liquid passage.

According to the third aspect of the invention, for the contents of various operations, verification of fine operations is enabled.

A fourth aspect of the invention is that with the first aspect of the invention, the detecting device has one or a plurality of light receiving devices, fixed or movably provided outside of the liquid passage, a movable region thereof or a part of the region, so as to have an optical axis directed theretowards.

Here, "light receiving device" is a photodiode, phototransistor, CdS or the like Furthermore, in the case where the liquid passage is movable, the light receiving device may be fixed. Moreover, in the case where the liquid passage is fixed and the container moves, the light receiving device should be movable with respect to the liquid passage.

According to the fourth aspect of the invention, by receiving light at one or a plurality of locations outside of the liquid passage, from the liquid passage, the movable region and the like, the optical condition of the liquid passage can be obtained from various directions, accurately and without contacting the liquid passage.

A fifth aspect of the invention is that with the fourth aspect of the invention, in the case where the liquid passage is capable of upward and downward movement, the light receiving devices are fixedly provided outside of the upward and downward movement path of the liquid passage such that the optical axis thereof is directed toward a predetermined height location of the upward and downward movement path.

Here, "predetermined height location" is for example, a location through which the lower end of the liquid passage and an upper level to which liquid can be stored, can be passed through by the transport device.

According to the fifth aspect of the invention, since the light receiving device can be fixed at a predetermined height location by utilizing the transport device of the liquid passage, it can be produced with a low cost, and simple construction.

A sixth aspect of the invention is that with either one of the fourth aspect of the invention and the fifth aspect of the invention, the detecting device has one or a plurality of light emitting devices which are fixed at or can move to a location for emitting light toward the liquid passage, a movable region thereof, or part of the region.

Here, the "light emitting device" is for example, an LED (light emitting diode), or a neon or tungsten lamp. Furthermore, the wavelength that the light emitting device emits may be near infrared light, and in the case of visible light of 600 nm or more, even with a low concentration of suspension, the light is transmitted with little attenuation.

Furthermore, the light emitting devices are provided at the location where the light receiving devices can detect light. For example, the location where the light emitting devices opposes the light receiving devices with the movement path or a part of the region therebetween, or a location where the light from the light emitting devices is reflected by the liquid passage and can be received by the light receiving devices.

According to the sixth aspect of the invention, by providing the light emitting device and emitting light therefrom, detection can be performed reliably and accurately and also, verification of various fine operations can be conducted depending on the liquid object.

A seventh aspect of the invention is that with the first aspect of the invention, the detecting device has an image pick up device for picking up images of the liquid passage, the movable region thereof or a part of the region, which is fixed or movably provided at a location capable of image pick up outside of the liquid passage or the movable region thereof Here, the "image pick up device" has a one-dimensional or two-dimensional CCD type or MOS type image sensor.

According to the seventh aspect of the invention, since by providing the image pickup device and the linear form light receiving device, the optical condition of a wide range of the region can be determined wholly and at once and detected promptly, detection and judgement can be done efficiently, promptly, and simply.

An eighth aspect of the invention is that with either one of the fourth aspect of the invention and the seventh aspect of the invention, the light receiving device or the image pick up device is provided in a line form spanning the maximum width of the transport path so as to be able to receive or to image pick up light from the maximum width of two or more of the liquid passages or the transport path of two or more of the liquid passages.

In the eighth aspect of the invention, an effect as already explained for the seventh aspect of the invention is demonstrated.

A ninth aspect of the invention is that with the eighth aspect of the invention, with the detecting device, the light emitting device spanning the maximum width is provided in linear form at an opposing location to the light receiving device with the liquid passage, the movable region thereof or a part of the region therebetween, such that light can be directed to the maximum width of two or more of the liquid passages or the transport path of two or more of the liquid passages.

In the ninth aspect of the invention, an effect as already explained for the seventh aspect of the invention is demonstrated.

A tenth aspect of the invention is that with the first aspect of the invention, the judgement device judges whether or not conditions related to the liquid passage corresponds to the instruction result, by analyzing the optical pattern composed of: the light amount, the light intensity or the image; the temporal fluctuations of the light amount, the light intensity or the image; or the spatial distribution of the light amount, the light intensity or the image. Here, "intensity" includes for example, illumination and brightness, detected by the detecting device According to the tenth aspect of the invention, the judgement device, by analyzing the optical pattern composed of: the light amount, the light intensity or image; temporal fluctuations of the light amount, light intensity or image; spatial distribution of the light amount, the light intensity or image; and the like detected by the detecting device, the condition related to the liquid passage can be judged precisely and finely.

An eleventh aspect of the invention is that with the tenth aspect of the invention, conditions related to the liquid passage include, the inaction or action status of the liquid passage, and physical or chemical inaction or fluctuation conditions of the contents of the liquid passage; the condition of the liquid passage includes, the presence of a liquid passage, the location of the liquid passage, the shape of the liquid passage, and the nature such as transparency; the physical condition of the contents of the liquid passage includes, the presence of liquid in the liquid passage, the presence of the surface or interface of the liquid in the liquid passage or the location thereof, the amount of the liquid in the liquid passage; the chemical condition of the contents in the liquid passage includes, the kind or nature such as viscosity of the liquid in the liquid passage, air bubbles in the liquid in the liquid passage or the presence of a suspension such as magnetic particles or the concentration thereof, the degree of suspension or mixing of the liquid in the liquid passage, or a reaction condition such as light emission.

The present invention also enables the verification of liquid suction and discharge, the presence of storage and/or agitation, the presence of separation by a magnetic device or the like, suction amount, discharge amount, storage amount, liquid condition (presence of suspension, mixing, reaction, flocculent, or precipitation, clarity, translucence, density, concentration, dilution, color and the like), and the like.

According to the eleventh aspect of the invention, since various kinds of condition related to the liquid passage can be judged, precise and detailed information can be obtained with a simple construction.

A twelfth aspect of the invention is that with either one of the sixth aspect of the invention and the ninth aspect of the invention, the judgment device judges, in the case of a light emitting level where the amount or intensity of the light received by the light receiving device is almost the same as the amount or intensity of the light from the light emitting device, that there is no liquid passage present, and in the case of a predetermined shielding level where the amount or intensity of the light received by the light receiving device is smaller than the amount or intensity of the light from the light emitting device, that a liquid passage is present.

According to the twelfth aspect of the invention, by simple analysis, the presence of the liquid passage can be judged with accuracy and high reliability.

A thirteenth aspect of the invention is that with the tenth aspect of the invention, the judgement device judges, based on a time difference between a time that the pressure control device is instructed to draw in a suction amount of liquid up to the height of the liquid passage and a time that the amount or intensity of the light detected by the detecting device actually changes, a condition of liquid flow resistance or a condition of blockage by foreign matter in the liquid passage.

According to the thirteenth aspect of the invention, because of the simple construction and analysis, various kinds of conditions can be judged.

A fourteenth aspect of the invention is that with the tenth aspect of the invention, the judgement device, after detecting the liquid surface, judges the condition of the liquid during the operation of suction into or discharge from the liquid passage, by analyzing the suction and discharge operation by a pressure control device, as well as the optical pattern composed of: the light amount, the light intensity or the image; temporal fluctuations of the light amount, the light intensity or the image; or spatial distribution of the light amount, the light intensity, or the image, detected by the detecting device.

Here, to detect the presence of liquid in the liquid passage, with the fourteenth aspect of the invention, the judgement device, in the case where the amount or intensity of the light received by the light receiving device is greater than the predetermined shielding level, but less than the light emitting level, and the transmissivity of the liquid to be drawn up is higher than in the liquid passage, judges that the liquid exists in the liquid passage. Moreover, the judgement device, in the case where the amount or intensity of the light received by the light receiving device is less than the predetermined shielding level, and the transmissivity of the liquid to be drawn up is lower than in the liquid passage, judges that liquid exists in the liquid passage.

According to the fourteenth aspect of the invention, the judgement device, after detecting the liquid surface, can judge the condition of the liquid during the operation of suction into or discharge from the liquid passage, by analyzing the suction and discharge operation by the pressure control device, as well as the pattern composed of the light amount, the light intensity or the image; temporal fluctuations of the light amount, the light intensity or the image; or spatial distribution of the light amount, the light intensity or the image, detected by the detecting device.

A fifteenth aspect of the invention is that with any one of the first aspect of the invention through the eleventh aspect of the invention, the judgement device, in the condition where the liquid is drawn up to lower than a predetermined height in the liquid passage, by raising the liquid passage or lowering the detecting device, judges the size of the volume drawn into the liquid passage, based on the distance moved to where the liquid surface in the liquid passage crosses the detecting location of the detecting device, and information showing the relationship between a predetermined optional distance from the suction aperture and the capacity of the liquid passage.

According to the fifteenth aspect of the invention, the judgement device, in the condition where the liquid is drawn up to lower than the predetermined height in the liquid passage, by raising the liquid passage, can judge the size of the volume drawn into the liquid passage, based on the distance raised to when the liquid surface in the liquid passage crosses the predetermined height, and information showing the relationship between a predetermined optional distance from the suction aperture and the capacity of the liquid passage.

A sixteenth aspect of the invention is that with any one of the first aspect of the invention through to the eleventh aspect of the invention, the judgement device, in the condition where the liquid is drawn into the liquid passage, by raising the liquid passage or lowering the detecting device, detects the liquid surface twice before it reaches the tip of the liquid passage, and also in the condition where the liquid is drawn up to a higher level than the predetermined height, by raising the liquid passage or lowering the detecting device, judges a liquid shortage in the case where a change is detected from the condition with liquid present to the condition with liquid again absent.

According to the sixteenth aspect of the invention, the judgement device, in the condition where the liquid is drawn into the liquid passage, by raising the liquid passage, detects the liquid surface twice before it reaches the tip of the liquid passage, and also in the condition where the liquid is drawn up to a higher level than the predetermined height, by raising the liquid passage, can judge a liquid shortage in the case where a change is detected from the condition with liquid present to the condition with liquid again absent.

A seventeenth aspect of the invention is that with any one of the first aspect of the invention through to the sixteenth aspect of the invention, the dispenser also has a magnetic device outside of the liquid passage capable of applying and removing a magnetic field to and from each liquid passage, and the operation instruction device also instructs the magnetic device to apply and remove a magnetic field, and the judgement device also judges the instruction result made by the magnetic field in relation to the liquid passage.

According to the seventeenth or thirty-fifth aspect of the invention, outside of the liquid passage, judgment can be made of the operation of the magnetic device capable of applying and removing a magnetic field to and from each liquid passage.

An eighteenth aspect of the invention is that with any one of the first aspect of the invention through to the seventeenth aspect of the invention, the liquid passage is a pipette tip detachably mounted on a nozzle provided on the dispenser, and the dispenser has a detaching device for the pipette tip, and the operation instruction device also gives the transport device and the detaching device an instruction to attach and detach the pipette tip, and the judgement device judges the result of the instruction of attaching and detaching the pipette tip.

According to the eighteenth aspect of the invention, the liquid passage is a pipette tip detachably mounted on a nozzle provided on the dispenser, and the detaching and attaching can also be verified.

A nineteenth aspect of the invention is that a dispenser operation verification apparatus according to any one of the first aspect of the invention through the eighteenth aspect of the invention, wherein a detection substance for aiding in or capable of detection by the detecting means, is contained in the liquid being sucked, discharged or stored in the liquid passages.

According to the nineteenth aspect of the invention, by adding a detection substance to a liquid, detection can be surely and accurately performed, and reliable verification of operations is enabled.

A twentieth aspect of the invention is that a dispenser comprising: one or a plurality of transparent or semi-transparent liquid passages capable of liquid suction, discharge and storage; a pressure control device for controlling the pressure in the liquid passage; a transport device for effecting relative movement between a container and the liquid passage; and an operation instruction device for issuing operating instructions to the pressure control device and the transport device, is used and verification of the operation of the dispenser is effected by having; an operating step for performing operations related to the liquid passage, a detection step for detecting an optical condition of the liquid passage, a movable region thereof or a part of that region, and a judgement step for judging the result of the instruction related to the liquid passage issued by the operation instruction device, based on the optical conditions detected by the detection step.

In the twentieth aspect of the invention, an effect as already explained for the first aspect of the invention is demonstrated.

A twenty-first aspect of the invention is that with the twentieth aspect of the invention, the judgement step judges the result of the instruction, based on information besides the optical condition, selected from amongst information containing; operation information related to the operation instructions of the operation instruction device, object information related to objects which the dispenser draws in, discharges and stores, and device information related to the dispenser including the liquid passage.

In the twenty-first aspect of the invention, an effect as already explained for the second aspect of the invention is demonstrated.

A twenty-second aspect of the invention is that with the twenty-first aspect of the invention, the operation information contains: suction amount or discharge amount; presence of suction or discharge; speed of suction or discharge; suction and discharge operation including time of suction or discharge; and/or information on movement operation including movement path, movement direction and/or movement distance, the object information contains the kind or nature of liquid and/or the type and/or the presence of suspensions such as magnetic particles and the like, and the device information contains the nature and shape of the liquid passage and/or information showing the relationship between the distance from a suction aperture and the capacity of the liquid passage.

In the twenty-second aspect of the invention, an effect as already explained for the third aspect of the invention is demonstrated.

A twenty-third aspect of the invention is that with the twentieth aspect of the invention, the detection step has a step for receiving light at one or a plurality of locations, from the liquid passage, the movable region or a part of the region.

In the twenty-third aspect of the invention, an effect as already explained for the fourth aspect of the invention is demonstrated.

A twenty-fourth aspect of the invention is that with the twenty-third aspect of the invention, in the case where the liquid passage is capable of upward and downward movement, and in the case where the light receiving device is fixedly provided outside of the upward and downward movement path of the liquid passage such that an optical axis thereof is directed toward a predetermined height location of the upward and downward movement path, the detecting step detects the lower edge of the liquid passage and up to the upper level to where the liquid can be stored while performing the upward and downward movement by the transport device.

In the twenty-fourth aspect of the invention, an effect as already explained for the fifth aspect of the invention is demonstrated.

A twenty-fifth aspect of the invention is that in either one of the twentieth aspect of the invention and the twenty-fourth aspect of the invention, the detection step is performed by receiving light emitted toward the liquid passage, the movable region or a part of the regions In the twenty-fifth aspect of the invention, an effect as already explained for the sixth aspect of the invention is demonstrated.

A twenty-sixth aspect of the invention is that with the twentieth aspect of the invention, the detecting step is performed by picking up an image of the liquid passage, a movable region thereof or a part of the region.

In the twenty-sixth aspect of the invention, an effect as already explained for the seventh aspect of the invention is demonstrated.

A twenty-seventh aspect of the invention is that with the twentieth aspect of the invention, the detecting step receives light spanning the maximum width of the upward and downward movement path so that the light from the maximum width of one or a plurality of the upward and downward movement paths of the liquid passage can be received or picked up.

In the twenty-seventh aspect of the invention, an effect as already explained for the seventh aspect of the invention is demonstrated.

A twenty-eighth aspect of the invention is that with the twentieth aspect of the invention, the detecting step shines light on the maximum width of one or a plurality of the upward and downward movement paths of the liquid passage.

In the twenty-eighth aspect of the invention, an effect as already explained for the seventh aspect of the invention is demonstrated.

A twenty-ninth aspect of the invention is that with the twentieth aspect of the invention, the judgement step judges whether or not conditions related to the liquid passage corresponds to the instruction result, by analyzing the optical pattern composed of: the light amount, the light intensity or the image; temporal fluctuations of the light amount, the light intensity or the image; or the spatial distribution of the light amount, the light intensity or the image, detected by the detecting step.

In the twenty-ninth aspect of the invention, an effect as already explained for the tenth aspect of the invention is demonstrated.

A thirtieth aspect of the invention is that with the twenty-ninth aspect of the invention, conditions related to the liquid passage in the judgment step include, the inaction or action status of the liquid passage, and physical or chemical inaction or fluctuation conditions of the contents of the liquid passage; the condition of the liquid passage includes, the presence of a liquid passage, the location of the liquid passage, the shape of the liquid passage, and the nature such as transparency; the physical condition of the contents of the liquid passage includes, the presence of liquid in the liquid passage, the presence of the surface or interface of the liquid in the liquid passage or the location thereof, the amount of the liquid in the liquid passage; the chemical condition in the liquid passage includes, the kind or nature such as viscosity of the liquid in the liquid passage, air bubbles in the liquid in the liquid passage or the presence of a suspension such as magnetic particles or the concentration thereof, the degree of suspension or mixing of the liquid in the liquid passage, or a reaction condition such as light emission.

In the thirtieth aspect of the invention, an effect as already explained for the eleventh aspect of the invention is demonstrated.

A thirty-first aspect of the invention is that with the twenty-fifth aspect of the invention, the judgment step judges, in the case of a light emitting level where the amount or intensity of the light received in the detecting step is almost the same as the amount or intensity of the light from light emission, that there is no liquid passage present, and in the case of a predetermined shielding level where the amount or intensity of the light received in the detecting step is smaller than the amount or intensity of the light from the light emission, that a liquid passage is present.

In the thirty-first aspect of the invention, an effect as already explained for the twelfth aspect of the invention is demonstrated.

A thirty-second aspect of the invention is that with the twentieth aspect of the invention, the judgment step judges, based on a time difference between a time that the pressure control device is instructed to draw in a suction amount of liquid up to the height of the liquid passage and a time that the amount or intensity of the light detected in the detecting step actually changes, a condition of liquid flow resistance or a condition of blockage by foreign matter in the liquid passage.

In the thirty-second aspect of the invention, an effect as already explained for the thirteenth aspect of the invention is demonstrated.

A thirty-third aspect of the invention is that with the twenty-ninth aspect of the invention, the judgement step, after detecting the liquid surface by the detection step, judges the condition of the liquid during the operation of suction into or discharge from the liquid passage, by analyzing a suction and discharge operation by a pressure control device, as well as an optical pattern composed of: the light amount, the light intensity or the image; temporal fluctuations of the light amount, the light intensity or the image; or spatial distribution of the light amount, the light intensity, or the image, detected in the detecting step.

In the thirty-fourth aspect of the invention, an effect as already explained for the fourteenth aspect of the invention is demonstrated.

A thirty-fourth aspect of the invention is that with the twentieth aspect of the invention, the judgement step, in the condition where the liquid is drawn up to lower than a predetermined height in the liquid passage, by raising the liquid passage or lowering the detecting device, judges the size of the volume drawn into the liquid passage, based on the distance moved to where the liquid surface in the liquid passage crosses the detecting location of the detecting device, and information showing the relationship between a predetermined optional distance from the suction aperture and the capacity of the liquid passage.

In the thirty-fourth aspect of the invention, an effect as already explained for the fifteenth aspect of the invention is demonstrated.

A thirty-fifth aspect of the invention is that with the twentieth aspect of the invention, the judgement step, in the condition where the liquid is drawn into the liquid passage, by raising the liquid passage or lowering the detecting device, detects the liquid surface twice before it reaches the tip of the liquid passage, and also in the condition where the liquid is drawn up to a higher level than the predetermined height, by raising the liquid passage or lowering the detecting device, judges a liquid shortage in the case where a change is detected from the condition with liquid present to the condition with liquid again absent.

In the thirty-fifth aspect of the invention, an effect as already explained for the sixteenth aspect of the invention is demonstrated.

A thirty-sixth aspect of the invention is that with any one of the twentieth aspect of the invention through to the thirty-fifth aspect of the invention, the dispenser also has a magnetic device outside of the liquid passage capable of applying and removing a magnetic field to and from each liquid passage, and the operation instruction device also instructs the magnetic device to apply and remove a magnetic field, and the judgement step also judges the instruction result made by the magnetic field in relation to the liquid passage.

In the thirty-sixth aspect of the invention, an effect as already explained for the seventeenth aspect of the invention is demonstrated.

A thirty-seventh aspect of the invention is that with any one of the twentieth aspect of the invention through to the thirty-sixth aspect of the invention, the liquid passage is a pipette tip detachably mounted on a nozzle provided on the dispenser, and the dispenser has a detaching device for the pipette tip, and the operation instruction device also gives the transport device and the detaching device an instruction to attach and detach the pipette tip, and the judgement step judges the result of the instruction of attaching and detaching the pipette tip.

In the thirty-seventh aspect of the invention, an effect as already explained for the eighteenth aspect of the invention is demonstrated.

A thirty-eighth aspect of the invention is that with any one of the twentieth aspect of the invention through the thirty-seventh aspect of the invention, further comprises a step of adding a detection substance for aiding in or capable of detection, to the liquid being sucked, discharged or stored in the liquid passage before the detection step.

In the thirty-eighth aspect of the invention, an effect as already explained for the nineteenth aspect of the invention is demonstrated.

BRIEF DESCRIPTION OF THE DRAWINGS

FIG. 4 is a diagram showing the principal parts of the dispenser according to the embodiment of the present invention.

FIG. 6 is diagram for explaining of a tip presence verification operation by the detecting device according to the embodiment of the present invention.

FIG. 7 is diagram for explaining of a liquid amount verifying operation by the detecting device according to the embodiment of the present invention.

FIG. 12 is diagram for explaining a liquid amount shortage verification operation by the detecting device according to the embodiment of the present invention.

BEST MODE FOR CARRYING OUT THE INVENTION

Next is a description of embodiments of the present invention based on the figures The present invention is not limited to these embodiments unless specified.

Figure 1:
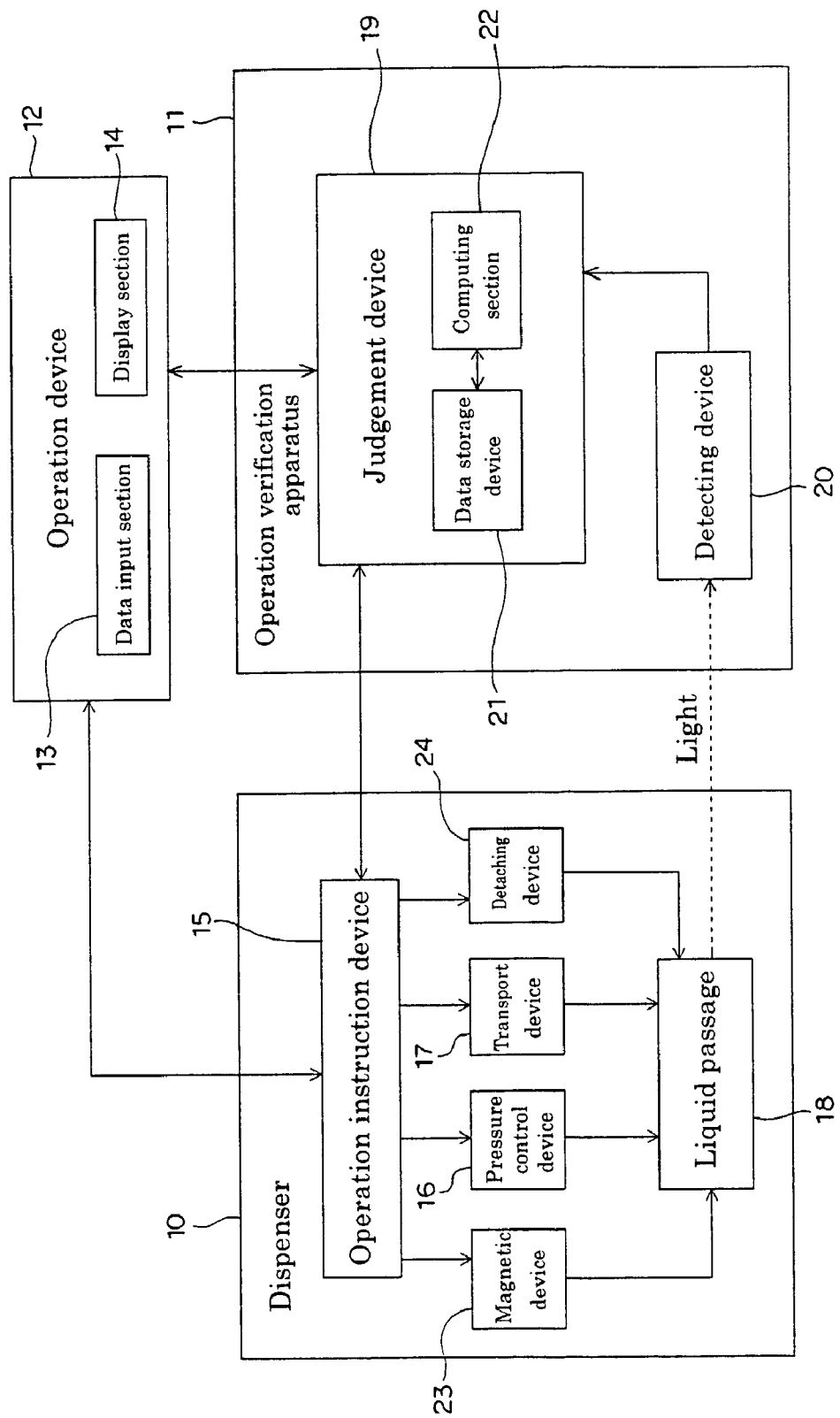
FIG. 1 is a block diagram showing the dispenser system according to the embodiment of the present invention.

FIG. 1 shows a dispenser system 1 according to the present embodiments.

This dispenser system 1 comprises; a dispenser 10 which dispenses liquid by drawing up and discharging liquid stored in a container, an operation verification apparatus 11 for verifying the operation of the dispenser 10, and an operation device 12 for effecting input of various operation instructions and data with respect to the dispenser 10 and the operation verification apparatus 11, and also for displaying contents of operating instructions, and the result of the operation verification and the like for an operator.

Here, the operation device 12 comprises; a data input section 13 including a keyboard, switches, a mouse, a touch panel, a communication device, a CD drive, a floppy disk drive or the like for entering the operation instructions and data, and a display section 14 comprising a CRT, an LCD panel, a plasma display or the like.

The dispenser 10 comprises: one or a plurality of transparent or semi-transparent liquid passages 18 capable of liquid suction, discharge and storage; a pressure control device 16 for controlling the pressure in the liquid passage 18; a transport device 17 for performing upward and downward movement or horizontal movement of the liquid passage 18 in relation to a container; a magnetic device 23 provided outside of the liquid passage 18, capable of applying and removing a magnetic field to and from the liquid passage; a detaching device 24 for, in the case where the liquid passage 18 is constituted by a pipette tip detachably mounted on a nozzle in the dispenser 10, detaching the liquid passage 18 from the nozzle; and an operation instruction device 15 comprising: a CPU for issuing operation instructions to the pressure control device 16, the transport device 17, the magnetic device 23 and the detaching device 24. The operation instruction to be issued to the operation instruction device 15 is entered by the operator using the operation device 12.

The operation verification apparatus 11 has;: a detecting device 20 for detecting the optical condition of the liquid passage 18, a movable region thereof or a part of the region; and a judgement device 19, for judging, based on the optical condition detected by the detecting device 20, the result of the instruction related to the liquid passage 18 issued by the operation instruction device 15, and outputting the result to the display section 14 or other output device which is included in the operation device 12, for example, a printing device, a communication device, a floppy disc or the like, and optionally executing instructions for feedback to the operation instruction device 15 based on the result.

The judgement device 19 has a data storage section 21 comprising a memory device, a hard disc, an external memory device or the like, and a computing section 22 comprising a CPU, a sequencer or the like. The data storage section 21 stores, in advance or by entry from the operation device 12, information selected from amongst operation information related to the operation instruction from the operation instruction device 15, object information related to; the object that the dispenser draws in, discharges or stores, and device information related to the dispenser including the liquid passage. The computing section 22, based on the optical condition detected by the detecting device 20, the information selected from amongst the information stored in the data storage section 21, the operation information directly obtained from the operation instruction device 15, or the information input from the data input section 13, by computing, judges the condition related to the liquid passage. The computing section 22, for example, when making judgements, judges based on the object information or the device information stored in the data storage section 21 and input from the data input section 13, by comparing a standard optical condition obtained previously or by computing with the optical condition detected by the detecting device 20.

As follows is a more detailed description of each constituent.

Figure 2:
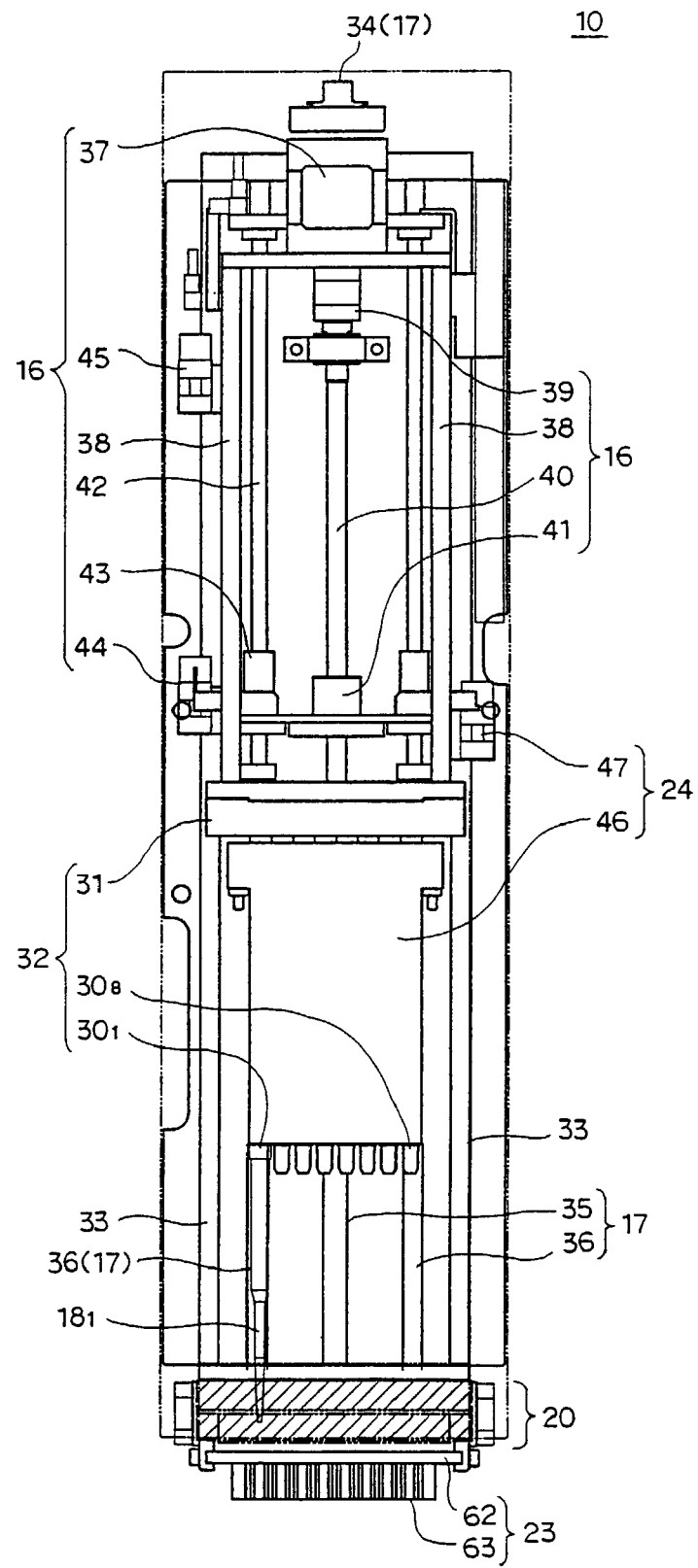
FIG. 2 is an overall structural diagram of the dispenser according to the embodiment of the present invention.

FIG. 2 is a front view showing a dispenser 10 according to the present embodiment.

The dispenser 10 has a plurality of sets (in this example, 8) of nozzles $30_1$–$30_8$, and a plurality of pipette tips $18_1$ (although there are 8 sets, sets $18_2$–$18_8$ are omitted from the figure for simplification) serving as transparent or semi-transparent liquid passages 18 attached to the lower ends of the nozzles $30_1$–$30_8$.

In the figure, there is provided beneath the pipette tips $18_1$, a magnetic device 23 capable of applying and removing a magnetic field to and from each of the pipette tips $18_1$–$18_8$ when the pipette tips $18_1$ are lowered. The magnetic device 23 has a permanent magnet 63 for applying a magnetic field to the interior of each of the pipette tips $18_1$–$18_8$ from the outside, and a slide plate 62 capable of sliding the permanent magnet 63 backward and forward (in the figure) to approach or recede from the pipette tips $18_1$–$18_8$. Furthermore, as shown by the hatching in the figure, a detecting device 20 of the operation verification device 11 for verify the operation of the dispenser 10, is located just above the magnetic device 23 The pipette tips $18_1$–$18_8$ comprise: a small diameter part and a large diameter part; or a small diameter part, an intermediate diameter part and a large diameter part, and the magnetic device 21 is for applying a magnetic field to the small diameter part or the intermediate diameter part.

The nozzles $30_1$–$30_8$ are installed in an 8-set nozzle unit 32 with an 8-set nozzle block base 31 supporting them. Each of the pipette tips $18_1$–$18_8$, attached to the lower end of the nozzles $30_1$–$30_8$ installed in the 8-row nozzle unit 32, is moved up and down by the transport device 17, relative to a base member 33 (column in the figure) of the dispenser 10, which supports the container, the detecting device 20 and the magnetic device 23 The transport device 17 comprises a pulley 34 driven by a stepper motor serving as a driving source (not shown in the figure), a ball screw 35 driven by a rotation force from the pulley 34, and a slide pipe 36 for guiding the upward and downward movement in the vertical direction. The 8-set nozzle unit 32 in which the nozzles $30_1$–$30_8$ and the like are installed, is moved up and down by the rotational drive of the ball screw 35.

Furthermore, a plunger (not shown in the figure), is installed in the nozzles $30_1$–$30_8$, so as to be slidable up and down, for the suction and discharge operations by controlling the pressure inside of the pipette tips $18_1$–$18_8$. A stepper motor 37, serving as a drive source for driving the plunger is fixedly provided on the 8-set nozzle block base 31 by means of a supporting member 38 provided upright from the 8-set nozzle block base 31 of the 8-set nozzle unit 32. The rotating spindle of the stepper motor 37 is connected to a ball screw 40 via a coupling 39. A nut 41 is threaded onto the ball screw 40 so that the 8 set plungers is supported on a nut 41. Moreover, with the nut 41 there is provided a sliding bush 43, and the sliding bush 43, which slidingly mates with a slide pipe 42, guides the movement of the plunger up and down.

In the figure, numeral 44 denotes an origin sensor for detecting the origin of the upward and downward movement of the plunger, and numeral 45, denotes a limit sensor for the plunger operation. Both are installed on the column 33. Here, the stepper motor 37, the ball screw 40 and the like correspond to the pressure control device 16.

In the figure, numeral 46 denotes a tip off plate for detaching the pipette tips $18_1$–$18_8$ from the nozzles $30_1$–$30_8$, and numeral 47 denotes a tip off verification sensor for verifying the detachment of the pipette tips $18_1$–$18_8$. These constitute the detaching device 24. Here, the whole of the dispenser 10 is stored inside of a casing provided with an opening in a lower part of a front face so that the pipette tips $18_1$–$18_8$ can be observed from outside.

Figure 3:
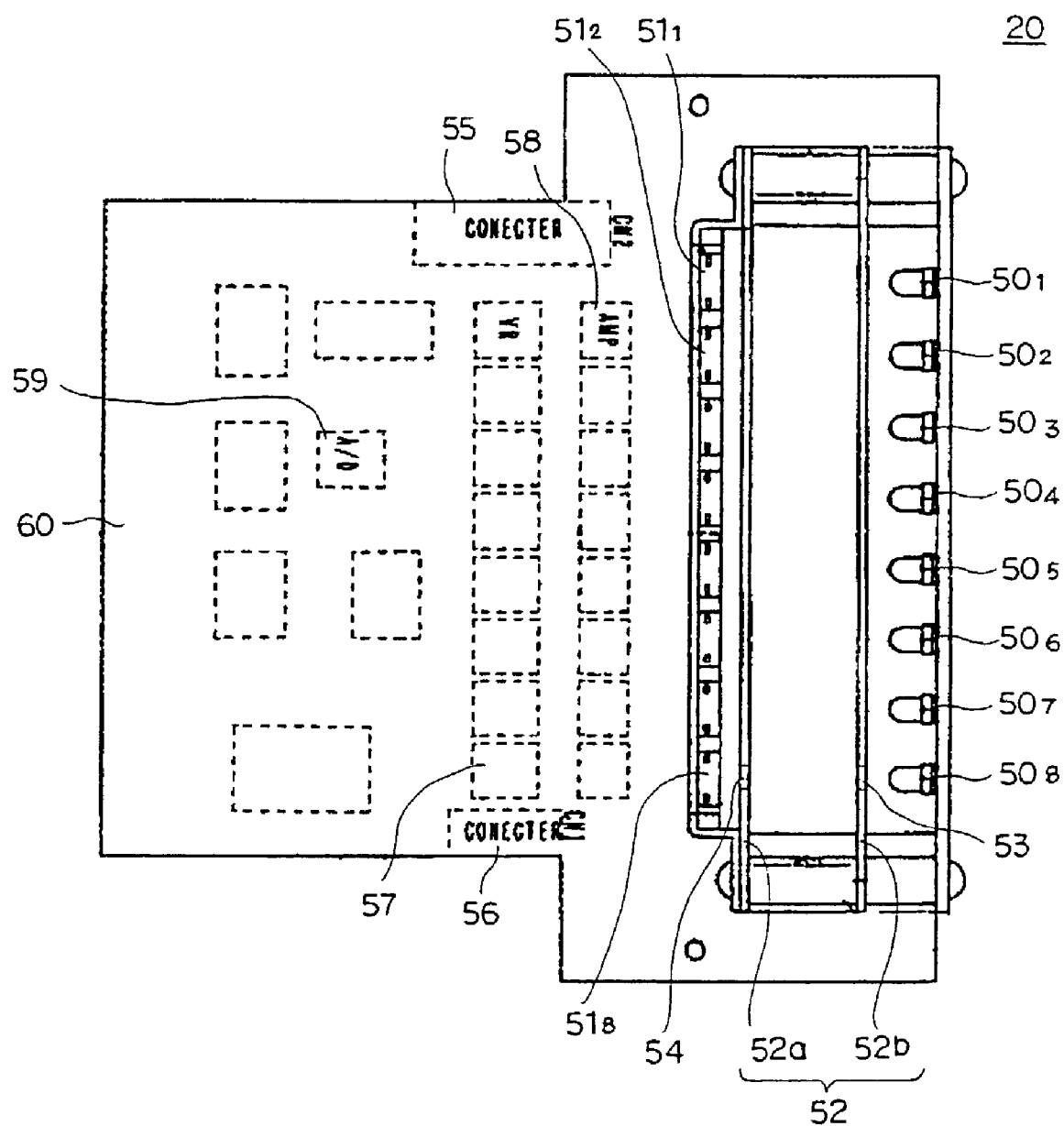
FIG. 3 is a diagram showing a detecting device according to the embodiment of the present invention.

FIG. 3 shows the details of an optical sensor unit serving as the detecting device 20 according to the present embodiment. As shown in FIG. 3, the detecting device 20, which is an optical sensor, comprises light emitting elements $50_1$–$50_8$ using LEDs, and light receiving elements $51_1$–$51_8$ using photo diodes. These light emitting elements $50_1$–$50_8$ and light receiving elements $51_1$–$51_8$ are provided at a predetermined height corresponding to outside of an upward and downward movement path corresponding to a movable region of each of the pipette tips $18_1$–$18_8$, so as to form respective pairs on either side of the path for each of the pipette tips $18_1$–$18_8$. Here, "predetermined height" is a location through which the lower end of the pipette tips $18_1$–$18_8$ and up to an upper level to where the liquid can be stored, can be passed through by the transport device 17.

The light emitting elements $50_1$–$50_8$ and the light receiving elements $51_1$–$51_8$ are fixed to a supporting member 52. Sufficient space is provided between opposite sides 52a and 52b of the supporting member 52 for the pipette tips $18_1$–$18_8$ to pass through. Pairs of holes 54 and 53 are made, one in each side 52a and 52b along the optical axis for each transport path of the pipette tips $18_1$–$18_8$.

Furthermore on a base 60 of the detecting device 20, as shown in FIG. 3, an amplifier 58 for amplifying the light detected by the detecting elements $51_1$–$51_8$, a control connector 55, a power connector 56, a gain adjustment trimmer 57 and an A/D converter 59 are respectively provided.

FIG. 4(a) is an external plan view of the detecting device 20, and FIG. 4(b) is a side view of the lower part of the dispenser 10.

The slide plate 62 of the magnetic device 23 is supported and slides in a channel 64 provided on a side plate 61 made of aluminum or the like. Near a front edge of the slide plate 62, a drip receiver 65 is fitted, which is a shaped hollow or tray for receiving drips from the ends of the pipette tips $18_1$–$18_8$. A rack 66 is provided to the rear of the slide plate 62 and meshed with a pinion 67. The pinion 67 is fixed to the same spindle as that of a belt pulley which is connected to a rotating spindle of a motor 69 via a belt 68, and thus rotated by the motor 69. Here, in the figure, numeral 70 denotes a sensor cover. In FIG. 4(a), parts covered by the sensor cover 70 are shown by perspective. Besides, numeral 71 denotes a position sensor for the slide plate 62. Numeral 72 denotes a member for supporting the side plate 61 and so on.

With the above construction, the results of the various operation instructions issued to the pressure control device 16, the transport device 17, the magnetic device 23, and the detaching device 24 are judged based on the optical condition detected by the detecting device 20. The obtained result of the judgement is, for example, displayed on the screen of the display section 14 to inform the user.

Figure 5:
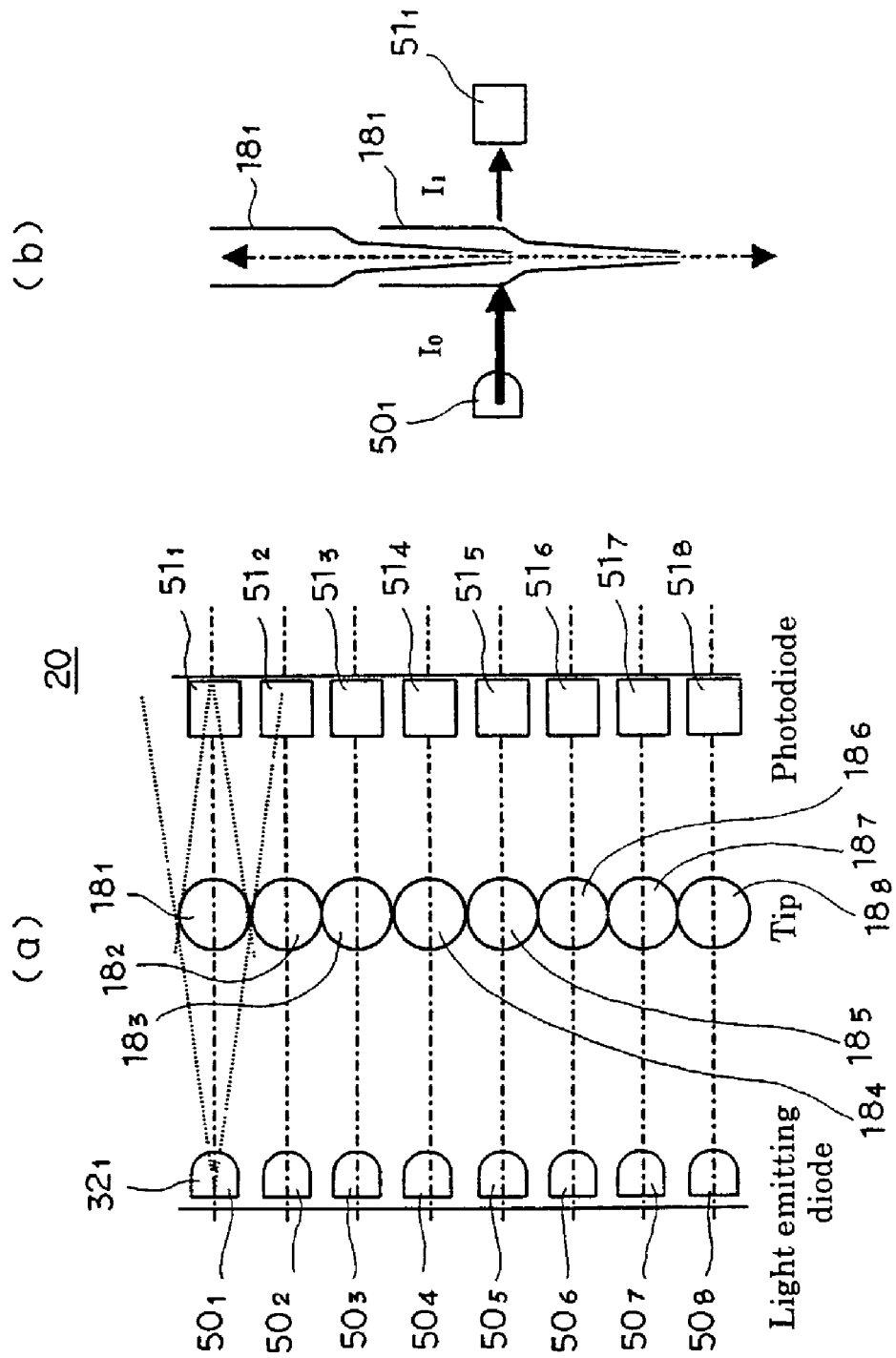
FIG. 5 is diagram for explaining the detecting device function according to the embodiment of the present invention.

FIG. 5(a) is a plan view showing the principle outline of the detecting device 20 according to this embodiment, and FIG. 5(b) is a side view. The detecting device 20 comprises light emitting elements $50_1$–$50_8$ and light receiving elements $51_1$–$51_8$. The light emitting elements $50_1$–$50_8$ and the light receiving elements $51_1$–$51_8$ are set in opposing locations to each other along the optical axes shown by dotted lines in the figure for each of the pipette tips $18_1$–$18_8$, outside of the upward and downward transport path of the pipette tips $18_1$–$18_8$, with the path of the pipette tips $18_1$–$18_8$ therebetween.

The pipette tips $18_1$–$18_8$ (hereafter with subscripts omitted), as shown in FIG. 5(a), move upward and downward, and the light emitting elements $50_1$–$50_8$ (hereafter with subscripts omitted) and the light receiving elements $51_1$–$51_8$ (hereafter with subscripts omitted) are fixedly provided at a predetermined height location of the upward and downward transport path.

FIG. 6 shows the case where the detecting device 20 judges the presence of the pipette tip 18 to verify the operation.

FIG. 6(a) shows the case where the tip 18 is not attached. In this case the light from the light emitting element 50 is observed without change as light amount $I_0$ by the light receiving element 51 as shown in the optical pattern in FIG. 6(c). In the case where the tip 18 is attached as in FIG. 6(b), the result is that the light from the light emitting element 50 is absorbed and scattered, and light amount $I_1$ is observed by the light receiving element 50 as shown in the optical pattern in FIG. 6(c). The judgement device 19, by comparing the operation instruction and the detected optical pattern, instructs the display section 14 to display affirmative or negative.

FIG. 7 shows the case where the presence of liquid in the pipette tip 18 is judged to verify the operation.

FIG. 7(a) shows the condition when liquid is not drawn into the pipette tip 18. In this case, because the air in the tip 18 has a low refractive index, all of the light from the light emitting element 50, passing through the tip cannot be collected since the lens effect is not large, and as shown in the optical pattern in FIG. 7(c), the light amount $I_1$ is received.

Conversely, as shown in FIG. 7(b), in the condition when liquid is drawn into the pipette tip 18, the light of the light emitting element 50 converges according to the same principle as for a cylindrical lens since there is liquid with a high refractive index in the tip 18 As a result, as shown in the optical pattern in FIG. 7(c), a far higher light amount $I_2$ is received compared to the light amount $I_1$ for the case with no liquid inside. Here the above description has been for the case of liquid with high light transmissivity.

On the other hand, in the case of liquid with low light transmissivity, in other words a liquid with high light absorption, most of the light passing through the tip 18 is absorbed. Therefore, as shown in the optical pattern in FIG. 7(d), for the light intensity or light amount observed, a light amount $I_2$, which is lower than the light intensity or light amount $I_1$ for the case where there is no liquid is observed. Accordingly, in the case where the liquid is known in advance to have low light transmissivity, the presence of the liquid can be judged by observing the low light amount.

Furthermore, liquid such as a suspension of small beads or blood serum can be reliably detected using the lens effect, by selecting visible light where the wavelength of the light of the light emitting element is 600 nm or more to prevent absorption by the liquid.

Moreover, in the case where whole blood or a suspension with an extremely high concentration of beads is used, the lens effect and light extinction by absorption counteract, which sometimes makes it difficult to detect. In this case, by dissolving a coloring matter in the solution that absorbs the wavelength of the light source being used, the light amount is decreased to less than $I_0$, enabling accurate detection. In this way, in the case where the nature of the liquid being drawn up is known in advance, it is possible to detect accurately by the change in the observed value, that the liquid is drawn up.

Figure 8:
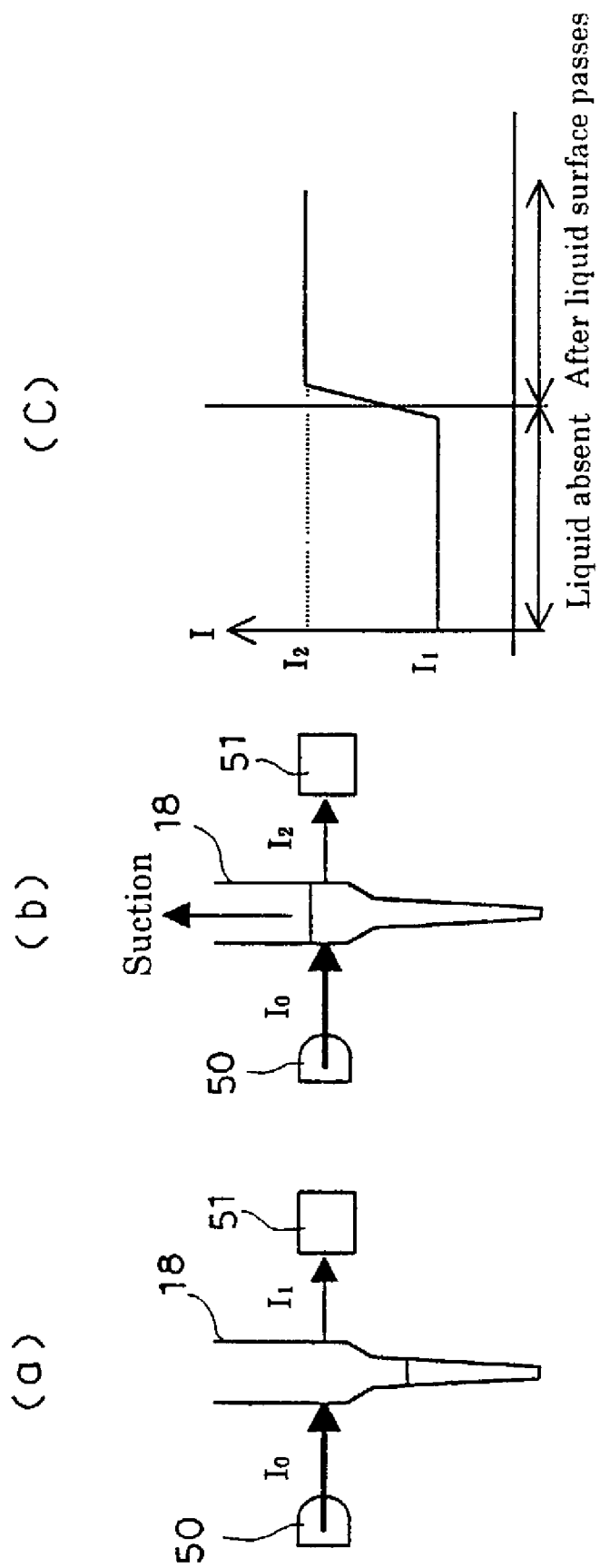
FIG. 8 is diagram for explaining of a draw up verification operation by the detecting device according to the embodiment of the present invention.

FIG. 8 shows the case where the detecting device 20 judges the passing of the liquid surface in the pipette tip 18, to verify the operation.

In the case where, in the condition where the height of the tip is fixed and a high light transmissivity liquid such as a reagent or the like is drawn up, then as shown in FIG. 8(a), in the condition where the liquid surface does not go past the sensor axis, the light intensity is low, as shown in FIG. 8(c). Immediately after the liquid surface passes through, as shown in FIG. 8(b), the light intensity or the light amount increases as shown in the optical pattern in FIG. 8(c). Accordingly, if a change in the light amount is observed during the drawing up operation, it can be judged that the time of the change is the time when the liquid surface passes. On the other hand, in the case where a low light transmissivity liquid is drawn up, immediately after the liquid surface passes, the light intensity or the light amount decreases.

Figure 9:
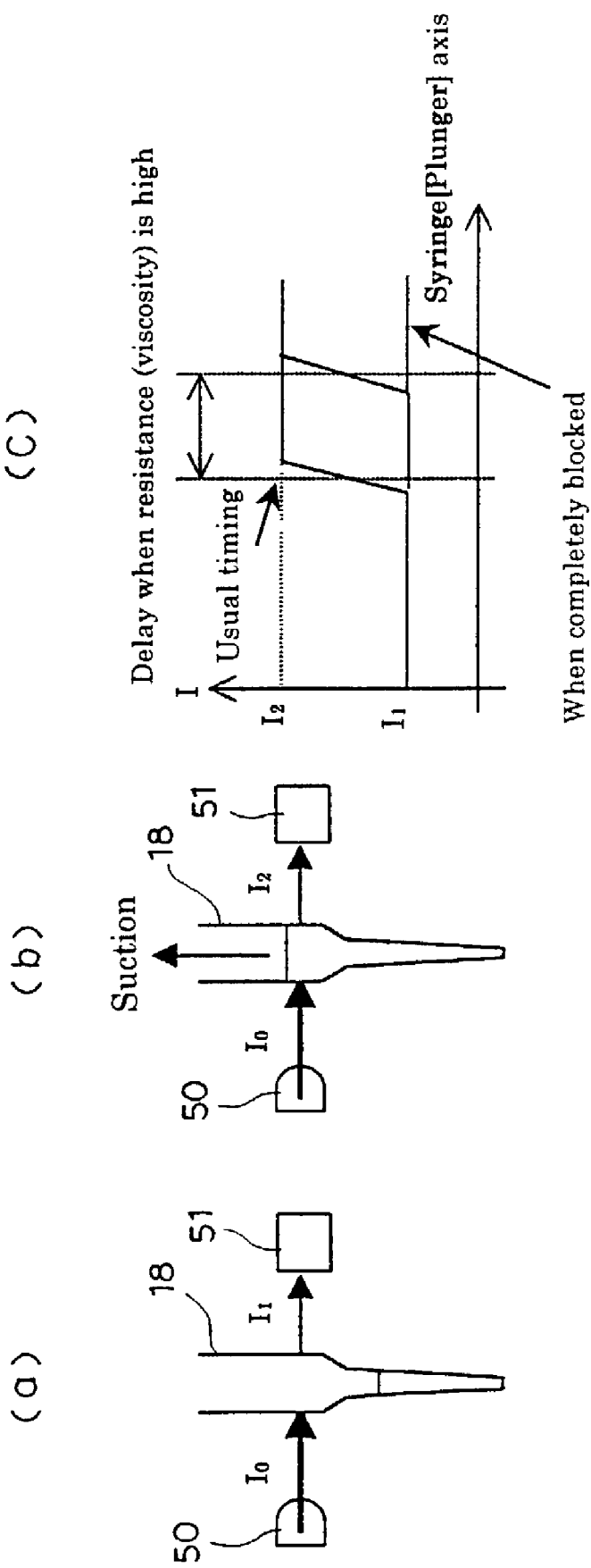
FIG. 9 is diagram for explaining of a tip blockage verification operation by the detecting device according to the embodiment of the present invention.

FIG. 9 shows the case where the liquid flow resistance or viscosity is judged, to verify the operation.

In this case, if the drawn up amount when the liquid surface in the tip 18 is on the optical axis is measured in advance, the flow resistance of the configuration can be known from a correlation of the passing through of the liquid surface and the operation position of the plunger.

In the case where the liquid is drawn up using the pressure control device 16, the timing of the passing through of the liquid surface is delayed more when drawing up a high viscosity liquid than a low viscosity liquid like water, as shown in the optical pattern in FIG. 9 (c). Also in the case of drawing up water, when the end of the tip is pressed to the bottom of the liquid container or the end of the tip is blocked with foreign matter, the timing is delayed. In the case where the tip is completely blocked, the liquid surface cannot be detected however strongly the pressure control device 16 is operated.

Figure 10:
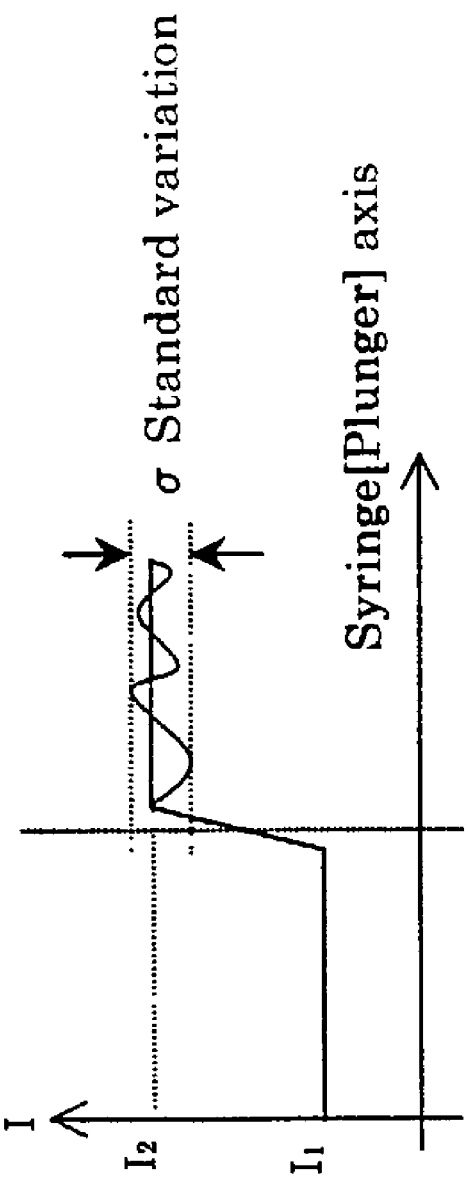
FIG. 10 is diagram for explaining of a foam (or the like) verification operation by the detecting device according to the embodiment of the present invention.

FIG. 10 shows the case where the detecting device 20 detects the presence of foam or flocculent or suspension in the liquid drawn into the pipette tip 18.

As shown in FIG. 10(a), in the case where a flocculent such as foam, protein or the like is mixed in a liquid such as a reagent or the like, then since as shown in the optical pattern in FIG. 10(b), the suction and discharge operation by the pressure control device 16 as well as the measurement data fluctuate greatly, the intermixing can be detected by the fluctuation value after detecting the liquid surface. Moreover, after the liquid is drawn up, by repeating the suction and discharge operation by the pressure control device 16, the fluctuation amount of the measured value can be obtained.

Figure 11:
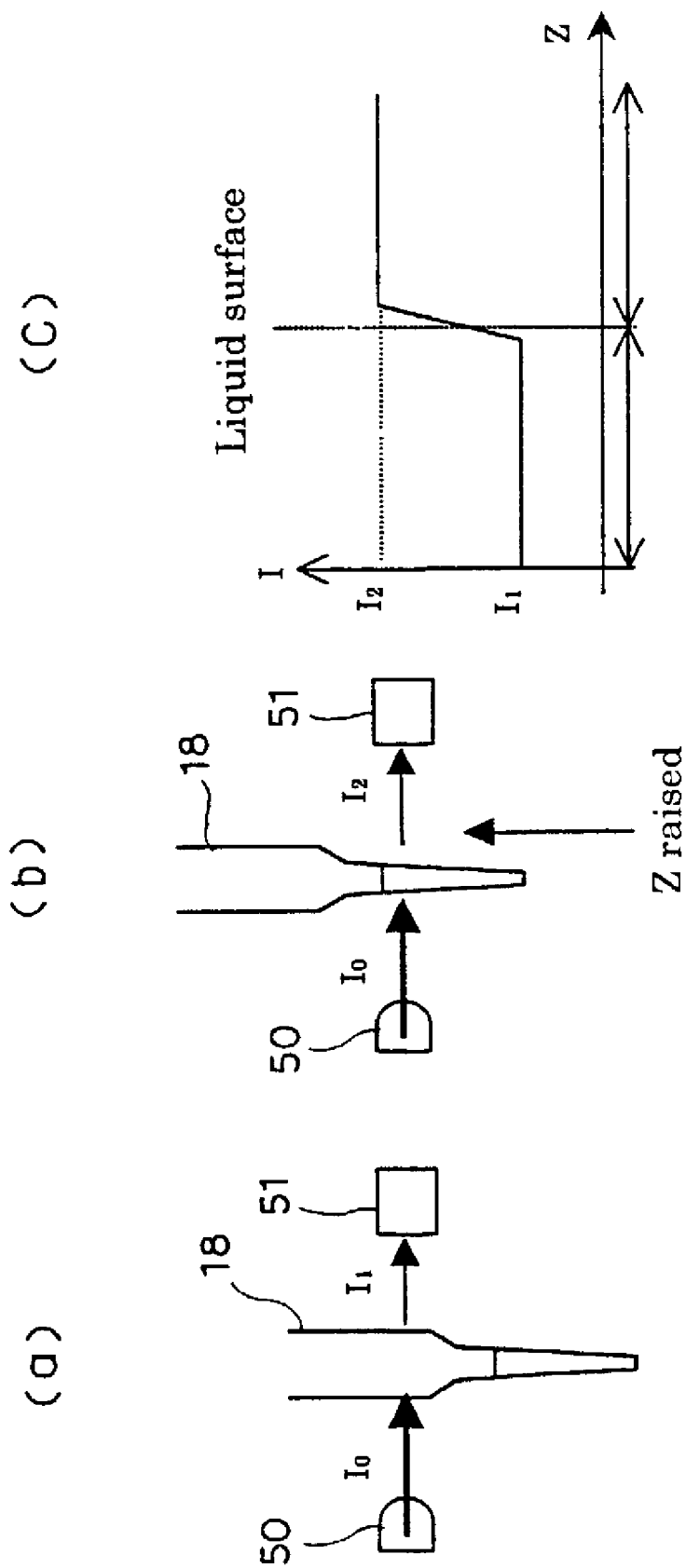
FIG. 11 is diagram for explaining of a draw up verification operation by the detecting device according to the embodiment of the present invention.

FIG. 11 shows the case where the detecting device 20 verifies the liquid amount drawn into the pipette tip 18.

In the condition with the liquid drawn up to below the sensor optical axis as shown in FIG. 11(a), when the pipette tip 18 is moved upward, then as shown in FIG. 11(b), at a certain time the liquid surface inside the tip 8 crosses the optical axis. As shown in the optical pattern in FIG. 11(c), by comparing the Z-axis coordinate when the sensor detects the liquid level, with translation data for the Z-axis coordinate and the liquid amount obtained in advance and stored in the data storage section 21, the liquid amount in the tip 18 can be determined.

FIG. 12 shows the case where the detecting device 20 can verify a shortage in the liquid amount of the liquid drawn into the pipette tip 18.

As shown in FIG. 12(a), in the case where the liquid drawn up is insufficient, air enters the end of the tip 18. Accordingly, in the condition where a reagent is drawn up, then as shown in FIG. 12(b), if the pipette tip 18 is moved upward along the Z axis, the two liquid surfaces are detected before reaching the end of the tip 18. That is to say, in the condition where the liquid is drawn up to the sensor optical axis or higher, if the Z axis is moved upward, then as shown in the optical pattern in FIG. 12(c), the condition changes from the condition for the presence of a reagent back to the condition for the absence of a reagent.

In the case where the liquid which the pipette tip 18 draws up according to the embodiment is semi-transparent with respect to the observing light source, this is also applicable. In the case of a semi-transparent liquid, depending on the light transmissivity, light convergence by the lens effect and light extinction by absorption and scattering counteract so that there is a possibility of difficulty in clearly distinguishing the light amount of the tip 18 itself. In this case, by mixing in advance in the liquid to be drawn up, coloring matter that has sufficient absorption for the wavelength to be observed, enables an accurate distinction Each of the above-described embodiments is described specifically for the purpose of better understanding the present invention, and does not exclude other embodiments. Accordingly, modification is possible within the scope in which the gist of the invention is not changed. For example, in the above explanation, the nozzle and pipette tip are movable up and down by the transport device, and the detecting device is described for the case where the light emitting element and light receiving element are fixed. However, the nozzle and the pipette tip may be movable horizontally as well, and it is also possible for the nozzle and the pipette tip to be fixed and for only the container to move. In that case, the light emitting element and the light receiving element of the detecting device would be movable. Furthermore, the light that the light emitting element emits is described for the case of visible light, however, it is not restricted to the case of visible light, and infrared light, ultraviolet light or the like can be used. Moreover, by fitting a filter in front of the light emitting device, it is possible to emit various wavelengths of light.

Furthermore, according to the above explanation, the light emitting device and the light receiving device are used as the detecting device, however, it is possible to use an image pick-up device. Moreover, in the above explanation, the verification of the operation by the magnetic device is not explained, however, it is possible to verify the result of applying and removing a magnetic field by the magnetic device. The above example is described for the case where a pipette tip is detachably mounted on a nozzle, however, it is possible that the nozzle itself is a transparent or semi-transparent liquid passage without a pipette tip.

According to the above explanation, the judgement result is described only in the case of displaying this on the display section to inform the operator, however, it is possible to inform by other means such as an alarm sound, voice or the like. Furthermore, it is possible, based on the judgement result obtained, to use feedback to control the operation, by sending a signal to the operation instruction device 15.

Moreover, in the above explanation, the light emitting device of the detecting device is limited to one kind, however, it is possible to emit light by selecting from a plurality of light emitting device depending on the object of the verification such as the liquid type or the like, by instructions from the operation section, or to insert and remove a plurality of filters between the light emitting device and the liquid passage. Furthermore, in the above explanation, as the magnetic device, a magnet provided so as to be able to approach and recede from the pipette tip is used, however, it is possible to use a means whereby turning an electromagnet on or off applies and removes a magnetic field to and from inside the liquid passage. Moreover, the invention is not limited to the 8-set nozzles, and by providing two or more of the light receiving device or image pick-up device, it is also applicable to a dispenser in which the nozzles are arrayed in matrix form.

The invention claimed is:

1. A dispenser operation verification apparatus, wherein with a dispenser comprising: one or a plurality of transparent or semi-transparent liquid passages capable of liquid suction, discharge and storage; pressure control means for controlling the pressure in the liquid passage; transport means for effecting relative movement between a container and the liquid passage; and operation instruction means for issuing operating instructions to said pressure control means and said transport means, the operation of said dispenser is verified by providing;

detecting means for detecting an optical condition of contents of said liquid passage, a movable region thereof or a part of that region, and judgement means for judging the result of the instruction related to an operation of agitation by sucking and discharging the liquid into or from the liquid passage respectively issued by the operation instruction means, based on the optical conditions of the contents of the liquid passage detected by said detecting means, and instructing to the operation instruction means based on the result of the judgement, wherein said judgement means judges whether or not conditions related to the contents of the liquid passage correspond to the instruction result, by analyzing an optical pattern composed of: the light amount, the light intensity or the image; temporal fluctuations of the light amount, the light intensity or the image; or the spatial distribution of the light amount, the light intensity or the image, detected by said detecting means.

2. A dispenser operation verification apparatus according to claim 1, wherein said judgement means, is adapted to judge the result of the instruction based on information besides said optical condition, said information selected from amongst information containing; operation information related to the operation instructions of said operation instruction means, object information related to objects which said dispenser draws in, discharges and stores, and device information related to said dispenser including the liquid passage.

3. A dispenser operation verification apparatus according to claim 2, wherein said operation information contains: suction amount or discharge amount; presence of suction or discharge; speed of suction or discharge; suction and discharge operation including time of suction or discharge; and/or information on movement operation including movement path, movement direction and/or movement distance, said object information contains the kind or nature of liquid and/or the type and/or the presence of suspensions such as magnetic particles and the like, and said device information contains the shape of the liquid passage and/or information showing the relationship between the distance of a surface of a liquid being drawn up in said liquid passage from a suction aperture and the volume of said liquid.

4. A dispenser operation verification apparatus according to claim 1, wherein said detecting means has one or a plurality of light receiving means, fixed or movably provided outside of said liquid passage or a movable region thereof, so as to have an optical axis directed towards said liquid passage, the movable region thereof or a part of the region.

5. A dispenser operation verification apparatus according to claim 1, wherein in the case where said liquid passage is capable of upward and downward movement along an upward and downward movement path, said light receiving means is fixedly provided outside of the upward and downward movement path of said liquid passage such that the optical axis thereof is directed toward a predetermined height location along the upward and downward movement path.

6. A dispenser operation verification apparatus according claim 4, wherein said detecting means has one or a plurality of light emitting means fixedly or movably provided at a location for emitting light toward said liquid passage, a movable region thereof, or part of the region.

7. A dispenser operation verification apparatus according to claim 4, wherein said light receiving means is linearly arranged, spanning the maximum width of the transport path of said liquid passage so as to be able to receive light from the maximum width of two or more of the liquid passages or the transport path of two or more of the liquid passages.

8. A dispenser operation verification apparatus according to claim 7, wherein with said detecting means, said light emitting means spans the maximum width of the transport oath of said liquid passages and is linearly arranged at an opposing location to said light receiving means with said liquid passage, the movable region thereof or a part of the region therebetween, such that light can be directed to the maximum width of two or more of the liquid passages or the transport path of two or more of the liquid passages.

9. A dispenser operation verification apparatus according to claim 1, wherein the conditions related to the contents of the liquid passage include the concentration of air bubbles or a suspension such as magnetic particles in the liquid passage, the degree of suspension or mixing of the liquid in the liquid passage, or a reaction condition such as light emission.

10. A dispenser operation verification apparatus according to claim 6, wherein, in the case of a light emitting level where the amount or intensity of the light received by said light receiving means is almost the same as the amount or intensity of the light from said light emitting means, said judgment means judges that there is no liquid passage present, and wherein, in the case of a predetermined shielding level where the amount or intensity of the light received by said light receiving means is smaller than the amount or intensity of the light from said light emitting means, said judgment means judges that a liquid passage is present.

11. A dispenser operation verification apparatus according to claim 1, wherein, based on a time difference between a time that said pressure control means is instructed to draw in a suction amount of liquid up to a predetermined height of said liquid passage and a time that the amount or intensity of the light detected by said detecting means actually changes, said judgment means judges a condition of liquid flow resistance or a condition of blockage by foreign matter in said liquid passage.

12. A dispenser operation verification apparatus according to claim 1, wherein said judgement means judges the condition of the liquid during the operation of suction into or discharge from the liquid passage, by analyzing a suction and discharge operation by pressure control means, as well as an optical pattern composed of the light amount, the light intensity or the image; temporal fluctuations of the light amount, the light intensity or the image; or spatial distribution of the light amount, the light intensity, or the image, detected by said detecting means.

13. A dispenser operation verification apparatus according to claim 5, wherein, in the condition where the liquid is drawn up to lower than a predetermined height in said liquid passage by using the transport means to raise said liquid passage or lower said detecting means, said judgement means judges the size of the volume drawn into said liquid passage, based on the distance moved to where the liquid surface in said liquid passage crosses the detecting location of said detecting means, and information showing the relationship between a predetermined optional distance of a surface of the liquid being drawn up in said liquid passage from said suction aperture and the volume of said liquid.

14. A dispenser operation verification apparatus according to claim 5, wherein, in the condition where the liquid is drawn into said liquid passage, by raising said liquid passage or lowering said detecting means, said judgement means detects the liquid surface twice before it reaches a tip of the liquid passage, and wherein, in the condition where the liquid is drawn up to a higher level than said predetermined height by using the transport means to raise said liquid passage or lower said detecting means, said judgement means judges a liquid shortage in the case where a change is detected from a condition with liquid present to a condition with liquid again absent.

15. A dispenser operation verification apparatus according to claim 1, wherein said dispenser also has magnetic means outside of said liquid passage capable of applying and removing a magnetic field to and from each liquid passage, and said operation instruction means is adapted to instruct said magnetic means to apply and remove a magnetic field, and said judgement means is adapted to judge the instruction result made by said magnetic field in relation to the liquid passage.

16. A dispenser operation verification apparatus according to claim 1, wherein said liquid passage is a pipette tip detachably mounted on a nozzle provided on the dispenser, and said operation instruction means is adapted to give said transport means and said detaching device an instruction to attach and detach the pipette tip, and said judgement means is adapted to judge the result of the instruction of attaching and detaching the pipette tip.

17. A dispenser operation verification apparatus according to claim 1, wherein a coloring matter is contained in the liquid being sucked, discharged or stored in the liquid passages, the coloring matter having the absorption maximum nearby the wave length of the light from an emission means or an optical source or a suspension agent capable of dispersing insoluble solid substances within the liquid.

18. A dispenser operation verification method, wherein a dispenser comprising: one or a plurality of transparent or semi-transparent liquid passages capable of liquid suction, discharge and storage; pressure control means for controlling the pressure in the liquid passage; transport means for effecting relative movement between a container and the liquid passage; and operation instruction means for issuing operating instructions to said pressure control means and said transport means, is used and verification of the operation of the dispenser is effected by having;

an operating step for performing operations related to said liquid passage, a detection step for detecting an optical condition of said liquid passage a movable region thereof or a part of that region, and a judgement step for judging the result of the instruction related to an operation of agitation by sucking and discharging the liquid into or from the liquid passage respectively issued by said operation instruction means, based on the optical conditions of the contents of the liquid passage detected by said detection step and instructing to the operation instruction means based on the result of the judgement;

wherein said judgement step judges whether or not conditions related to the liquid passage corresponds to the instruction result, by analyzing the optical pattern composed of: the light amount, the light intensity or the image; temporal fluctuations of the light amount, the light intensity or the image; or the spatial distribution of the light amount, the light intensity or the image, detected by said detecting step.

19. A dispenser operation verification method according to claim 18, wherein said judgement step judges the result of the instruction, based on information besides said optical condition, selected from amongst information containing; operation information related to the operation instructions of said operation instruction means, object information related to objects which said dispenser draws in, discharges and stores, and device information related to said dispenser including the liquid passage.

20. A dispenser operation verification method according to claim 19, wherein said operation information contains: suction amount or discharge amount; presence of suction or discharge; speed of suction or discharge; suction and discharge operation including time of suction or discharge; and/or information on movement operation including movement path, movement direction and/or movement distance, said object information contains the kind or nature of liquid and/or the type and/or the presence of suspensions such as magnetic particles and the like, and said device information contains the nature and shape of the liquid passage and/or information showing the relationship between the distance from a suction aperture and the capacity of said liquid passage.

21. A dispenser operation verification method according to claim 18, wherein said detection step has a step for receiving light at one or a plurality of locations, from said liquid passage, said movable region or a part of the region.

22. A dispenser operation verification method according to claim 21, wherein in the case where said liquid passage is capable of upward and downward movement, and in the case where said light receiving means is fixedly provided outside of the upward and downward movement path of said liquid passage such that an optical axis thereof is directed toward a predetermined height location of the upward and downward movement path, said detecting step detects the lower edge of the liquid passage and up to the upper level to where the liquid can be stored while performing the upward and downward movement by said transport means.

23. A dispenser operation verification method according to claim 18, wherein said detection step is performed by receiving light emitted toward said liquid passage, the movable region or a part of the regions.

24. A dispenser operation verification method according to claim 18, wherein said detecting step is performed by picking up an image of said liquid passage, a movable region thereof or a part of the region.

25. A dispenser operation verification method according to claim 18, wherein said detecting step receives light spanning the maximum width of the upward and downward movement path so that the light from the maximum width of one or a plurality of the upward and downward movement paths of said liquid passage can be received or picked up.

26. A dispenser operation verification method according to claim 18, wherein said detecting step shines light on the maximum width of one or a plurality of the upward and downward movement paths of said liquid passage.

27. A dispenser operation verification method according to claim 18, wherein conditions related to the condition of the liquid passage includes, the concentration of air bubbles or a suspension such as a magnetic particles in the liquid passage, the degree of suspension or mixing of the liquid in the liquid passage, or a reaction condition such as light emission.

28. A dispenser operation verification method according to claim 23, wherein said judgment step judges, in the case of a light emitting level where the amount or intensity of the light received in said detecting step is almost the same as the amount or intensity of the light from light emission, that there is no liquid passage present, and in the case of a predetermined shielding level where the amount or intensity of the light received in said detecting step is smaller than the amount or intensity of the light from said light emission, that a liquid passage is present.

29. A dispenser operation verification method according to claim 18, wherein said judgment step judges, based on a time difference between a time that said pressure control means is instructed to draw in a suction amount of liquid up to a predetermined height of said liquid passage and a time that the amount or intensity of the light detected in said detecting step actually changes, a condition of liquid flow resistance or a condition of blockage by foreign matter in said liquid passage.

30. A dispenser operation verification method according to claim 18, wherein said judgement step, after detecting the liquid surface by said detection step, judges the condition of the liquid during the operation of suction into or discharge from the liquid passage, by analyzing a suction and discharge operation by pressure control means, as well as an optical pattern composed of: the light amount, the light intensity or the image; temporal fluctuations of the light amount, the light intensity or the image; or spatial distribution of the light amount, the light intensity, or the image, detected in said detecting step.

31. A dispenser operation verification method according to claim 18, wherein said judgement step, in the condition where the liquid is drawn up to lower than a predetermined height in said liquid passage, by raising said liquid passage or lowering said detecting means, judges the size of the volume drawn into said liquid passage, based on the distance moved to where the liquid surface in said liquid passage crosses the detecting location of said detecting means, and information showing the relationship between a predetermined optional distance from said suction aperture and the capacity of said liquid passage.

32. A dispenser operation verification method according to claim 18, wherein said judgement step, in the condition where the liquid is drawn into said liquid passage, by raising said liquid passage or lowering said detecting means, detects the liquid surface twice before it reaches the tip of the liquid passage, and also in the condition where the liquid is drawn up to a higher level than said predetermined height, by raising said liquid passage or lowering said detecting means, judges a liquid shortage in the case where a change is detected from a condition with liquid present to a condition with liquid again absent.

33. A dispenser operation verification method according to claim 18, wherein said dispenser also has magnetic means outside of said liquid passage capable of applying and removing a magnetic field to and from each liquid passage, and said operation instruction means also instructs said magnetic means to apply and remove a magnetic field, and said judgement step also judges the instruction result made by said magnetic field in relation to the liquid passage.

34. A dispenser operation verification method according to claim 18, wherein said liquid passage is a pipette tip detachably mounted on a nozzle provided on the dispenser, and said dispenser has a detaching device for the pipette tip, and said operation instruction means also gives said transport means and said detaching device an instruction to attach and detach the pipette tip, and said judgement step judges the result of the instruction of attaching and the pipette tip.

35. A dispenser operation verification method according to claim 18, further comprises a step of adding a coloring matter having the absorption maximum nearby the wave length of the light from an emission means or an optical source or a suspension agent capable of dispersing insoluble solid substance with the liquid for aiding in or capable of detection, to the liquid being sucked, discharged or stored in the liquid passage before the detection step.

* * * * *

UNITED STATES PATENT AND TRADEMARK OFFICE
CERTIFICATE OF CORRECTION

| | |
|---|---|
| PATENT NO. | : 7,160,510 B2 |
| APPLICATION NO. | : 10/169474 |
| DATED | : January 9, 2007 |
| INVENTOR(S) | : Hideji Tajima et al. |

It is certified that error appears in the above-identified patent and that said Letters Patent is hereby corrected as shown below:

On The Title Page, Item (54)
In the Title:

change "OPERATION CHECKING DEVICE AND CHECKING METHOD FOR DISPENSER" to --DISPENSER OPERATION VERIFICATION APPARATUS AND VERIFICATION METHOD--

Column 20, line 12, change "oath" to --path--

Signed and Sealed this

Sixth Day of November, 2007

JON W. DUDAS
*Director of the United States Patent and Trademark Office*